United States Patent [19]

Thatcher et al.

[11] Patent Number: 5,807,847
[45] Date of Patent: Sep. 15, 1998

[54] NITRATE ESTERS

[75] Inventors: Gregory R. J. Thatcher; Brian M. Bennett, both of Kingston, Canada

[73] Assignee: Queen's University at Kingston, Kingston, Canada

[21] Appl. No.: 658,145

[22] Filed: Jun. 4, 1996

[51] Int. Cl.[6] .................... C07C 38/102; C07C 203/04; A61K 31/255; A61K 31/66; A61K 31/39; A61K 31/21; C07F 9/40; C07D 327/04

[52] U.S. Cl. .................. 514/129; 514/23; 514/24; 514/439; 514/517; 514/509; 536/18.7; 536/55; 549/40; 558/175; 558/480; 558/484; 558/485; 560/309

[58] Field of Search ..................... 514/129, 439, 514/509, 517; 549/40; 558/175, 480, 484, 485; 560/309

[56] References Cited

U.S. PATENT DOCUMENTS

| 4,801,596 | 1/1989 | Simon et al. . |
| 4,863,949 | 9/1989 | Simon et al. . |
| 5,049,694 | 9/1991 | Bron et al. . |
| 5,284,872 | 2/1994 | Sandrock et al. . |
| 5,428,061 | 6/1995 | Sandrock et al. . |

FOREIGN PATENT DOCUMENTS

| 764461 | 8/1967 | Canada . |
| 792246 | 8/1968 | Canada . |
| 2075988 | 8/1991 | Canada . |
| 2158368 | 9/1994 | Canada . |
| 362575 | 4/1995 | European Pat. Off. . |
| 451760 | 9/1995 | European Pat. Off. . |
| 51-125750 | 11/1976 | Japan . |
| 01-304353 | 12/1989 | Japan . |
| 1-304353 | 12/1989 | Japan . |
| WO94/06428 | 3/1994 | WIPO . |
| 9500477 | 1/1995 | WIPO . |

OTHER PUBLICATIONS

Database CAPLUS on STN, Chemical Abstracts Service, (Columbus, Ohio), Acc. No. 1990:430989, JP 01–304353 (Sumitomo Chemical), abstract, 1990.
Database CAPLUS on STN, Chemical Abstracts Service, (Columbus, Ohio), Acc. No. 1977:166380, JP 51–125750 (Misato et al.), abstract, 1990.
Artz, J.D., Yang, K., Lock, J., Sanchez, C., Bennett, B.M., and Thatcher, G.R.J., "Reactivity of thionitrate ester: putative intermediates in nitrovasodilator activity", *Chem. Commun.* 927–928 (1996).

Bennett, B.M., McDonald, B.J., Nigam, R., and Simon, W.C., "Biotransformation of organic nitrates and vascular smooth muscle cell function", *Trends in Pharmacol. Sci.* 15: 245–249 (1994).
Cameron, D.R., Borrajo, A.M.P., Bennett, B.M., and Thatcher, G.R.J., "Organic nitrates, thionitrates, peroxynitrites, and nitric oxide: a molecular orbital study of $RXNO_2 \leftrightarrows RXONO$ (X=O,S) rearrangement, a reaction of potential biological significance", *Can. J. Chem.* 73: 1627–1638 (1995).
Chong, S., and Fung, H.–L., "Biochemical and pharmacological interactions between nitroglycerin and thiols. Effects of thiol structure on nitric oxide generation and tolerance reversal", *Biochem. Pharm.* 42: 1433–1439 (1991).
Feelisch, M., "Biotransformation to nitric oxide of organic nitrates in comparison to other nitrovasodilators", *Eur. Heart J.*, 14: 123–132 (1993).
Fung, H–L., "Nitrate therapy: is there an optimal substance and formulation" *Eur. Heart J.*, 12: 9–12 (1991).
Kojda, G., Feelisch, M., and Noack, E., "Sulfhydryl–containing nitrate esters: a new class of nitric oxide donors", *Cardiovasc. Drug Rev.* 13:275–288 (1995).
Yang, K., Artz, J.D., Lock, J., Sanchez, C., Bennett, B.M., Fraser, A.B., and Thatcher, G.R.J., "Synthesis of novel organic nitrate esters: guanylate cyclase activation and tissue relaxation", *J. Chem. Soc., Perkin Trans. 1*, 1073–1075 (1996).
Yeates, R.A., "Possible mechanisms of activation of soluble guanylate cyclase by organic nitrates", *Arzneim–Forsch./Drug Res.* 42(II): 1314–1317 (1992).
Yeates, R.A. Lauren, H., and Leitold, M., "The reaction between organic nitrates and sulfhydryl compounds", *Mol. Pharm.* 28: 555–559 (1985).
Zanzinger, J., Feelisch, M., and Bassenge, E., "Novel organic nitrates are potent dilators of large coronary arteries with reduced development of tolerance during long–term infusion in dogs: role of the sulfhydryl moiety", *J. Cardiovas. Pharm.*, 23: 772–778 (1994).

*Primary Examiner*—Michael G. Ambrose
*Attorney, Agent, or Firm*—Richard J. Hicks; Carol Miernicki Steeg

[57] ABSTRACT

Aliphatic Nitrate esters having a sulfur or phosphorus atom $\beta$ or $\gamma$ to a nitrate group having efficacy as vasodilators are described. Preferred nitrate esters may be synthesized by nitration of a 3-bromo-1,2-propanediol, and subsequent reaction to yield the desired mono, di or tetra nitrate ester.

7 Claims, No Drawings

NITRATE ESTERS

FIELD OF INVENTION

This invention relates to novel aliphatic nitrate esters and use thereof as nitro vasodilators. More particularly this invention relates to nitrate esters bearing a sulfur or phosphorus atom β or γ to a nitrate group which have therapeutic utility as vasodilators and nitric oxide pro-drugs and/or substitutes for nitroglycerin in therapy.

BACKGROUND OF INVENTION

Glyceryl trinitrate (GTN) or nitroglycerin has been used as a vasodilator in the treatment of angina pectoris for over a hundred years, and is now believed to exert its therapeutic effect through in-vivo release of nitric oxide (NO), which itself has been identified as Endothelium Derived Relaxing Factor (EDRF). Other organic nitrates, such as isosorbide dinitrate, have also been identified as effective and clinically important vasodilators. Unfortunately, the use of GTN is not without its disadvantages, a principal of which is the tolerance effect which builds up quite rapidly over a relatively short period of time and markedly reduces the efficacy of GTN as a vasodilator.

A substantial body of evidence supports the hypothesis that the vasodilatory activity of organic nitrates is largely the result of activation of guanylate cyclase (Gcase) leading to vascular smooth muscle relaxation. GTN must undergo biotransformation in vivo and it is proposed that tolerance development may be associated with this need for biotransformation; the exact mechanism of which remains unresolved. Proposed sulfhydryl-dependent pathways include enzymic and non-enzymic biotransformation by a thiol. Indeed, the non-enzymic interaction of GTN with a limited range of thiols such as cysteine, N-acetylcysteine and thiosalicylic acid leads to activation of Gcase with an $EC_{50}$ in the submillimolar range in vitro. Regardless of the exact mechanism of biotransformation of GTN in vivo, it is postulated herein that if sulfur-containing functionalities are incorporated into the structure of nitrate esters, such molecules have the potential to activate Gcase and release •NO without reliance on GTN biotransformation pathways. Based upon bioassay data it is postulated that phosphorus-containing functionalities so incorporated might have similar potential. Thus, there is a need for synthetic aliphatic nitrate esters containing sulfur or phosphorus functionalities that may substitute for nitroglycerin as therapeutic agents.

OBJECT OF INVENTION

It is an object of the present invention to provide novel aliphatic nitrate esters bearing a sulfur or phosphorus atom β or γ to a nitrate group.

Another object of the present invention is to provide methods for making the novel S or P-containing nitrate esters.

Yet another object of the present invention is to provide novel pro-drugs for use as vasodilators.

BRIEF DESCRIPTION OF INVENTION

By one aspect of this invention there is provided aliphatic nitrate esters containing at least one nitrate group, in which a S or P atom is situated β or γ to a nitrate group, having the general formula;

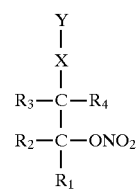

where X is $CH_2O$, NMe, S, $S_3M$, $PO_3HM$, $PO_3M_2$, SH, $SR_7$, $P(O)(OR_5)(OR_6)$, $P(0)(OR_5)(OM)$, $P(O)(OR_5)(R_6)$, $P(O)(OM)R_6$, $SO_2M$, $S(O)R_8$, $S(O)_2R_9$, $S(O)OR_8$ or $S(O)_2OR_9$;

Y is zero, $SR_4$, $SR_{10}$, $SSR_{10}$, $SO_2M$, $SO_3M$, $PO_3$ HM, $PO_3M_2$, $P(O)(OR_5)(OM)$, or $P(O)(OR_5)OR_6$;

$R_5$, $R_6$, $R_8$, $R_9$, $R_{10}$ are the same or different alkyls containing 1–12 carbon atoms or $C_1$ or $C_2$ connections to $R_1$–$R_3$ in cyclic derivatives;

$R_7$ is $C_1$–$C_8$ alkyl or acyl;

$R_2$ and $R_4$ are the same or different and selected from H, $ONO_2$, $C_1$–$C_4$ alkyl optionally bearing 1–3 nitrate groups, and acyl groups (—$C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is H, $Na^+$, $K^+$, $NH_4^+$ or $NH_nR_{7(4-n)}$, where n is 0–3.

By another aspect of this invention there is provided a pharmaceutical composition comprising an effective amount of an aliphatic nitrate ester having the formula

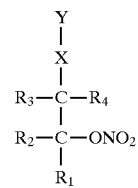

where X is $CH_2$, O, NH, NMe, S, $SO_3M$, $PO_3$ HM, $PO_3M_2$, SH, $SR_7$, $P(O)(OR_5)(OR_6)$, $P(0)(OR_5)(OM)$, $P(O)(OR_5)(R_6)$, $P(O)(OM)R_6$, $SO_2M$, $S(O)R_8$, $S(O)_2R_9$, $S(O)OR_8$ or $S(O)_2OR_9$;

Y is zero, $SR_4$, $SR_{10}$, $SSR_{10}$, $SO_2M$, $SO_3M$, $PO_3$ HM, $PO_3M_2$, or $P(O)(OR_5)(OM)$, $P(O)(OR_5)OR_6$;

$R_5$, $R_6$, $R_8$, $R_9$, $R_{10}$ are the same or different alkyls containing 1–12 carbon atoms or $C_1$ or $C_2$ connections to $R_1$ or $R_3$ in cyclic derivatives;

$R_7$ is $C_1$–$C_8$ alkyl or acyl;

$R_2$ and $R_4$ are the same or different and selected from H, $ONO_2$, $C_1$–$C_4$ alkyl optionally bearing 1–3 nitrate groups, and acyl groups (—$C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is H, $Na^+$, $K^+$, $NH_4^+$ or $Nh_nR_{7(4-n)}$, where n is 0–3.

in admixture with a physiologically acceptable carrier therefore.

By yet another aspect of this invention there is provided a method for effecting tissue relaxation in a patient in need thereof comprising administering to said patient an effective amount of an aliphatic nitrate ester having the formula:

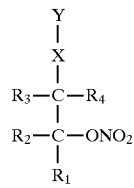

where X is $CH_2$, O, NH, NMe, S, $SO_3M$, $PO_3HM$, $PO_3M_2$, SH, $SR_7$, $P(O)(OR_5)(OR_6)$, $P(0)(OR_5)(OM)$, $P(O)(OR_5)(R_6)$, $P(O)(OM)R_6$, $SO_2M$, $S(O)R_8$, $S(O)_2R_9$, $S(O)OR_8$ or $S(O)_2OR_9$;

Y is zero, $SR_4$, $SR_{10}$, $SSR_{10}$, $SO_2M$, $SO_3M$, $PO_3HM$, $PO_3M_2$, $P(0)(OR_5)(OM)$, or $P(O)(OR_5)OR_6$;

$R_5$, $R_6$, $R_8$, $R_9$, $R_{10}$ are the same or different alkyls containing 1–12 carbon atoms or $C_1$ or $C_2$ connections to $R_1$ or $R_3$ in cyclic derivatives;

$R_7$ is $C_1$–$C_8$ alkyl or acyl;

$R_2$ and $R_4$ are the same or different and selected from H, $ONO_2$, $C_1$–$C_4$ alkyl optionally bearing 1–3 nitrate groups, and acyl groups (—$C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is H, $Na^+$, $K^+$, $NH_4^+$ or $NH_nR_{7(4-n)}$, where n is 0–3.

DETAILED DESCRIPTION OF PREFERRED EMBODIMENTS

Simple nitrate esters according to this invention contain one or more nitrate groups in which a S or P atom is situated β or γ to a nitrate group. Accordingly, a general formula for the esters of this invention is:

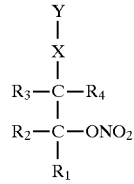

where X is $CH_2$, O, NH, NMe, S, $SO_3M$, $PO_3HM$, $PO_3M_2$, SH, $SR_7$, $P(O)(OR_5)(OR)$, $P(0)(OR_5)(OM)$, $P(O)(OR_5)(R_6)$, $P(O)(OM)R_6$, $SO_2M$, $S(O)R_8$, $S(O)_2R_9$, $S(O)OR_8$ or $S(O)_2OR$;

Y is zero, $SR_4$, $SR_{10}$, $SSR_{10}$, $SO_2M$, $SO_3M$, $PO_3HM$, $PO_3M_2$, $P(0)(OR_5)(OM)$, or $P(O)(OR_5)OR_6$;

$R_5$, $R_6$, $R_8$, $R_9$, $R_{10}$ are the same or different alkyls containing 1–12 carbon atoms or $C_1$ or $C_2$ connections to $R_1$ or $R_3$ in cyclic derivatives;

$R_7$ is $C_1$–$C_8$ alkyl or acyl;

$R_2$ and $R_4$ are the same or different and selected from H, $ONO_2$, $C_1$–$C_4$ alkyl optionally bearing 1–3 nitrate groups, and acyl groups (—$C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is H, $Na^+$, $K^+$, $NH_4^+$ or $NH_nR_{7(4-n)}$, where n is 0–3.

Compounds according to the present invention fall into five main categories having the formulae:

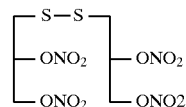

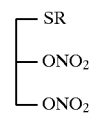

where R is $SO_3M$
and M is $Na^+$ or $K^+$

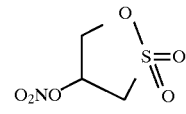

and

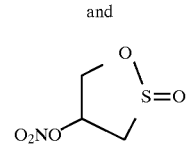

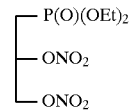

The compound of formula 1 was synthesized from 3-bromo-1,2-propanediol by dropwise addition into a cold mixture of nitric acid (68–70%, 4.0 eq) and sulfuric acid (95%, 4.0 eq) in methylene chloride $CH_2 Cl_2$ (50 ml) and reaction at room temperature for 30 minutes. The organic layer was separated, washed, dried and concentrated to yield a yellow oil which was purified by silica gel flash chromatography to give a 45% yield of 3-bromo-1,2,propanediol dinitrate,

was prepared by reacting compound 7 with an equimolar portion of $Na_2 S_2O_3$ in 3:1 $MeOH/H_2O$ at 50° C. for 10 hours and subsequently purifying by silica gel flash chromatography.

The Bunte salt 2 was oxidized with a small molar excess of hydrogen peroxide $H_2O_2$ (30%) in an ethanol: water mixture (1:1) with a catalytic amount of sulfuric acid for 2 days. Extraction with methylene chloride $CH_2 Cl2$, concentration, and purification by silica gel flash chromatography produced a 47% yield of the tetra-nitrate:

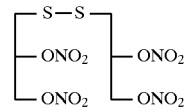

The $^{13}C$ NMR spectra of 1 and 2 revealed 6 and 3 signals respectively, as expected from the presence of two chiral centres in 1 and only one in 2 (Table 1). The H NMR spectra of glycerol dinitrate derivatives (1, 2, 6) are of interest because of the large geminal coupling at the nitrated methylene and small or unobservable geminal coupling at the other methylene position (Table 1).

In method 2, an Arbuzov reaction with 1-bromo-2,3-epoxypropane yields the 1-phosphono-2,3-epoxypropane, which is converted to the dinitrate 5 using the same procedure detailed for synthesis of 7. Isolation after chromatography yields the product 5 with: $^{31}P$ NMR $\delta=23$ ppm; $^{13}C$

TABLE 1

NMR, IR, m.p. and mass spec characteristics of nitrates 1–4[a]

| m.p. | $^1$H-NMR(ppm)[b] | $^{13}$C-NMR(ppm)[b] | IR(cm$^{-1}$) | MS(m/z, intensity %) |
|---|---|---|---|---|
| 1 Liquid | 5.43–5.55(2H, m), 4.84–8.93(2H, m), 4.60–4.69(2H, dd, J=6, 13Hz), 2.97–3.16(4H, m). | 77.08/77.00 69.33/69.29, 37.05/36.89. | (neat), 1634, 1270 1042, 995, 855. | (Cl, Cl$^-$), 429(M+Cl, 100), 393(M−1, 10). |
| 2 86° C.(dec.) | (DMSO-d$_6$), 5.75–5.80(1H, m), 4.99–5.07(1H, dd, J=3.13Hz), 4.77–4.86(1H, dd, J=6.13Hz), 3.20–3.23(2H, d, J=7Hz) | (DMSO-d$_6$), 79.02 70.97, 32.04 | (KBr), 1638, 1449, 1378, 1351, 1290, 1210, 1042, 654. | (ES$^+$, Na), 323(M+Na, 53). |
| 3 65–66° C. | 5.80–5.87(1H, m), 4.67–4.75(1H, dd, J=5, 11Hz), 4.50–4.57(1H, dd, J=2, 11Hz), 3.69–3.80(1H, dd, J=8, 15Hz), 3.35–3.44 (1H, dd, J=3, 15Hz). | 76.95, 69.88, 48.66 | (KBr), 1651, 1344, 1286, 1139, 937. | (Cl, Cl$^-$), 2.18 (M+Cl, 100). |
| 4 64–65° C. | 5.84–5.90(1H, m), 4.98–5.06(1H, dd, J=4, 12Hz), 4.77–4.83(1H, d, J=12Hz), 3.50–3.58(1H, dd , J=2, 15Hz), 3.31–3.42 (1H, dd, J=7, 15Hz). | 80.49, 75.07, 64.04 | (KBr), 1649, 1339, 1287, 1122, 926. | (Cl, Cl$^-$), 202(M+Cl, 100) |

[a]All compounds were characterized by elemental analysis or high resolution mass spec., hplc and NMR analysis for homogeneity.
[b]CDCl$_3$ was used as solvent for $^1$H—, $^{13}$C-NMR, unless otherwise indicated.

Nitration of bis-(2,3-dihydroxypropyl) disulfide

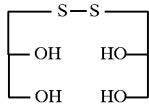

(7)

in the biphasic CH$_2$ Cl$_2$/aqueous HNO$_3$H$_2$SO$_4$ medium described above yielded, after chromatographic silica gel purification 5% and 10% yields of the sultone 3 and sultine 4, respectively. The anticipated tetra nitrate 1 was not obtained. NMR spectra obtained for these products were highly solvent-dependent and were similar to those of the glycerol dinitrates, but with the significant difference that the large geminal coupling is associated with the upfield rather than the downfield methylene protons (Table 1). Definitive structure identification rested upon mass spectral data: soft chemical ionization with Cl ion capture determined 3 and 4 to be the sultone and sultine, respectively.

The compound of formula 5 was synthesized by two methods. In the first method, 1-bromo-2,3-propanediol, 6, was silylated to provide a substrate for the Arbuzov reaction with triethyl phosphite. The resulting phosphonate was nitrated using nitronium tetrafluoroborate to yield the product 5, which was isolated after silica flash chromatography.

NMR $\delta=16, 27, 62, 71, 75$ ppm; $^1$H NMR $\delta=1.3, 2.2, 4.1, 4.4–5.0, 5.5$ ppm.

Activation of soluble Gcase by nitrates 1–4 was assayed, employing partially purified enzyme freshly prepared from rat aorta homogenates, using the radio immunoassay method described by Bennett et al, Can. J. Physiol. Pharmacol. 1992, 70, 1297, the disclosure of which is incorporated herein by reference.

Dose-response curves were obtained for Gcase activation by nitrates 1–4 and GTN in the presence and absence of cysteine and dithiothretol (DTT; both 2 mM). The data from these curves are summarized in Table 2, which gives: (a) concentrations of nitrates required to give a response equivalent to the maximal response seen for GTN+cysteine, and (b); the maximal response measured for each nitrate. The Gcase assay data shows that dinitrate 2 activates Gcase, with a submillimolar EC$_{50}$, in the absence of any added thiol, in contrast to GTN which requires added cysteine. Compounds 2 and 4 also activate Gcase in the presence of DTT in contrast to GTN. The activity of the tetra nitrate 1 is very low and entirely equivalent to glycerol-1,2-dinitrate in this assay. No activation of Gcase by glycerol mononitrates is observed in this assay.

TABLE 2

Summary of guanylyl cyclase activation dose response curves for nitrates 2–4 in presence and absence of thiols (2 mM) relative to GTN + 2 mM cysteine.

|  | GTN + cys | 2 no thiol | 2 + cys. | 2 + DTT | 3 + cys. | 4 + cys. | 4 + DTT |
|---|---|---|---|---|---|---|---|
| % maximal response[b] | 100(5) | 105(12) | 293(15) | 164(23) | 1087(200) | 98(16) | 174(30) |
| concentration at max. response (mM)[c] | 1.0 | 0.5 | 5.0 | 5.0 | 1.0 | 5.0 | 1.5 |

TABLE 2-continued

Summary of guanylyl cyclase activation dose response curves for nitrates 2–4 in presence and absence of thiols (2 mM) relative to GTN + 2 mM cysteine.

| | GTN + cys | 2 no thiol | 2 + cys. | 2 + DTT | 3 + cys. | 4 + cys. | 4 + DTT |
|---|---|---|---|---|---|---|---|
| GTN equivalence concentration(mM)[d] | 1.0 | 0.4 | 0.7 | 2.0 | 0.2 | 5.0 | 0.8 |

[a]Average of 4–6 experiments using 2–3 separate preparations. Various nitrates gave no response above basal concentrations: GTN, GTN + DTT, 1, 3, 3 + DTT, 4, glycerol-1,2-dinitrate + cysteine. Response to 1 (+DTT or +cys.) was discernible but <20%. Several responses do not plateau, thus $EC_{50}$ values cannot be quoted.
[b]Maximal response to GTN + cys. Ranged from 360–540 pmol/min.mg in separate experiments and was set at 100%. Other responses relative to maximal GTN + cys. response are expressed as percentages with standard errors.
[c]Nitrate concentration at which maximal response is observed: concentrations did not exceed 5 mM (1 mM for 3).
[d]Nitrate concentration at which response reaches maximal response to GTN + cysteine (ie. 100%).

In order to extend the Gcase data, the relaxing effects of nitrates 2,3 and 4 on rat aortic tissue were examined. Thoracic aortic strips were prepared from male Sprague-Dawley rats (Charles-River, Canada) as described in McGuire et al, J. Exp. Ther. 1994, 271,708 and Stewart et al, Can. J. Physiol Pharmacol 1989, 67, 403, incorporated herein by reference. Tissues were contracted submaximally with phenylephrine (0.1 $\mu$M) and exposed to various concentrations of nitro vasodilator to obtain concentration-response curves. Compared to the control experiments, in this intact tissue assay, all three nitrates were observed to cause significant tissue relaxation. The $EC_{50}$ values for 2,3 and 4 were 3.94 $\mu$M, 3.37 $\mu$M and 9.06 $\mu$M respectively. In similar rat aorta relaxation assays, a nitrosothiol (BU$^t$SNO) and GTN itself were seen to give $EC_{50}$ values of 5 $\mu$M and 8.3 nM, respectively.

Three of the four sulfur-containing nitrates described herein, two mononitrates (3,4) and one dinitrate (2), are shown to activate Gcase at a higher maximal even than GTN. In addition, compound 2 does not require added thiol for activation. The significant relaxing effects of 2,3 and 4 on rat aortic tissue are compatible with Gcase activation data. The positioning of a sulfur atom $\beta$ or $\gamma$ to the nitrate group may allow intramolecular interaction of S with the nitrate N via a five-membered ring.

We claim:

1. Aliphatic nitrate esters containing at least one nitrate group, in which a S or P atom is situated $\beta$ or $\gamma$ to a nitrate group, having the general formula:

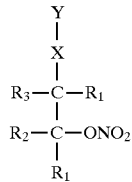

where X is $CH_2$, O, NH, NMe, S, $SO_3M$, $PO_3HM$, $PO_3M_2$, SH, $SR_7$, $P(O)(OR_6)(OR_6)$, $P(O)(OR_6)(OM)$, $P(O)(OR_5)(R_6)$, $P(O)(OM)R_6$, $SO_2M$, $S(O)R_8$, $S(O)_2R_9$, $S(O)OR_8$ or $S(O)_2OR_9$;

Y is $SR_4$, $SR_{10}$, $SSR_{10}$, $SO_2M$, $SO_3M$, $PO_3HM$, $PO_3M_2$, $P(O)(OR_5)(OM)$, or $P(O)(OR_5)(OR_6)$, or does not exist;

$R_5$, $R_6$, $R_8$, $R_9$, $R_{10}$, are the same or different alkyls containing 1–12 carbon atoms or $C_1$ or $C_2$ connections to $R_1$ or $R_3$ in cyclic derivatives;

$R_7$ is $C_1$–$C_8$, alkyl or acyl;

$R_2$ and $R_4$ are the same or different and selected from H, $ONO_2$, $C_1$–$C_4$ alkyl optionally bearing 1–3 nitrate groups, and acyl groups (—$C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is H, $Na^+$, $K^+$, $NH_4^+$ or $N^+H_nR_{11(4-n)}$, where n is 0–3; and with the proviso that, when $R_6$ is an alkyl group, and R, $R_2$ and $R_4$=H, $R_3$ is not H or methyl.

2. Aliphatic nitrate esters as claimed in claim 1 wherein:

X is selected from the group consisting of $CH_2$, O, NH, NMe, S, $SO_3M$, SO, $SO_2M$, $S(O)R_8$, $S(O)_2 R_9$, $S(O)OR_8$ and $S(O)_2 OR_9$; and Y is selected from the group consisting of zero, $SR_4$, $SR_{10}$, $SSR_{10}$, $SO_2M$ and $SO_3M$.

3. Aliphatic nitrate esters as claimed in claim 2, wherein Y does not exist.

4. Aliphatic nitrate esters as claimed in claim 1, having a formula selected from the group consisting of:

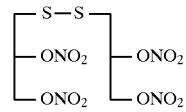

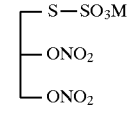

where M is $Na^+$ or $K^+$

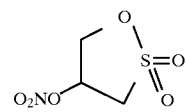

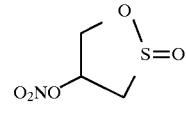

and

-continued

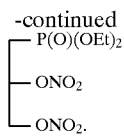

5. A pharmaceutical composition comprising an effective amount of an aliphatic nitrate ester having the formula:
where X is $CH_2$, O, NH, NMe, S, $SO_3M$, $PO_3HM$, $PO_3M_2$, SH, $SR_7$, $P(O)(OR_5)(OR_6)$, $P(O)(OR_6)(OM)$, $P(O)(OR_6)(R_6)$, $P(O)(OM)R_6$, $SO_2M$, $S(O)R_6$, $S(O)_2R_9$, $S(O)OR_8$ or $S(O)_2OR_9$;

Y is $SR_4$, $SR_{10}$, $SSR_{10}$, $SO_2M$, $SO_3M$, $PO_3HM$, $PO_3M_2$, $P(O)(OR_5)(OM)$, or $P(O)(OR_5)(OR_6)$, or does not exist;

$R_5$, $R_6$, $R_8$, $R_9$, $R_{10}$, are the same or different alkyls containing 1–12 carbon atoms or $C_1$ or $C_2$ connections to $R_1$ or $R_3$ in cyclic derivatives;

$R_7$ is $C_1$–$C_8$, alkyl or acyl;

$R_2$ and $R_4$ are the same or different and selected from H, $ONO_2$, $C_1$–$C_4$ alkyl optionally bearing 1–3 nitrate groups, and acyl groups ($—C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is $H$, $Na^+$, $K^+$, $NH_4^+$ or $N^+H_nR_{11(4-n)}$, where n is 0–3; and with the proviso that, when $R_6$ is an alkyl group, and $R_1$, $R_2$ and $R_4$=H, $R_3$ is not H or methyl;

in admixture with a physiologically acceptable carrier therefor.

6. A pharmaceutical composition as claimed in claim 5, wherein

X is selected from the group consisting $CH_2$, O, NH, NMe, S, $SO_3M$, SO, $SO_2M$, $S(O)R_8$, $S(O)_2R_9$, $S(O)OR$, or $S(O)_2OR_9$; and Y is selected from the group consisting of $SR_4$, $SR_{10}$, $SSR_{10}$, $SO_2M$, $SO_3M$, or does not exist.

7. A pharmaceutical composition as claimed in claim 5, wherein said nitrate ester has a formula selected from the group consisting of

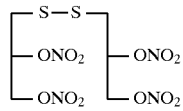

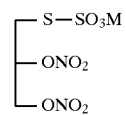

where M is $Na^+$ or $K^+$

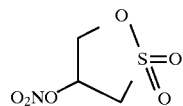

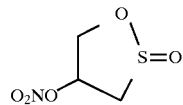

and

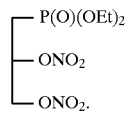

* * * * *

UNITED STATES PATENT AND TRADEMARK OFFICE
CERTIFICATE OF CORRECTION

PATENT NO. : 5,807,847                   Page 1 of 2

DATED : September 15, 1998

INVENTOR(S) : Gregory R. J. Thatcher and Brian M. Bennett

It is certified that error appears in the above-identified patent and that said Letters Patent is hereby corrected as shown below:

Column 2, line 11, "$CH_2O$, NMe, S, $S_3M$," should be --$CH_2$, O, NH, NMe, S, $SO_3M$,--.

Column 3, line 48, "SH, $SR_7$, $P(O)(OR_5)(OR)$," should be --SH, $SR_7$, $P(O)(OR_5)(OR_6)$,--.

Column 3, line 50, ",OR;" should be --,$OR_9$;--.

Column 6, Table 1, far right column, first entry, "(Cl, Cl$^-$)" should be --(Cl, Cl$^-$)--.

Column 6, Table 1, far right column, third entry, "(Cl, Cl$^-$)" should be --(Cl, Cl$^-$)--.

Column 6, Table 1, far right column, fourth entry, "(Cl, Cl$^-$)" should be --(Cl, Cl$^-$)--.

Column 6, Table 2, title, "cysteine." should be --cysteine."--.

Claim 1, after line 47,

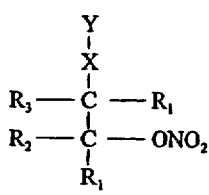

should be

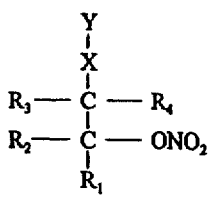

UNITED STATES PATENT AND TRADEMARK OFFICE
CERTIFICATE OF CORRECTION

PATENT NO. : 5,807,847

DATED : September 15, 1998

INVENTOR(S) : Gregory R. J. Thatcher and Brian M. Bennett

It is certified that error appears in the above-identified patent and that said Letters Patent is hereby corrected as shown below:

Claim 1, line 58, "P(O)(OR$_6$)(OR$_6$)," should be --P(O)(OR$_5$)(OR$_6$),--.

Claim 5, line 8, after "having the formula:" should be

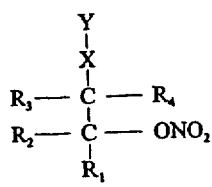

Claim 5, line 10, "P(O)(OR$_6$)(OM), P(O)(OR$_6$)" should be --P(O)(OR$_6$)(OM), P(O)(OR$_5$)--.

Claim 5, line 11, "S(O)R$_6$," should be --S(O)R$_8$,--.

Claim 6, line 38, "OR, or S(O)$_2$OR$_9$;" should be --OR$_4$, and S(O)$_2$OR$_9$;--.

Signed and Sealed this

Twenty-fifth Day of May, 1999

Q. TODD DICKINSON

*Attest:*

*Attesting Officer*     Acting Commissioner of Patents and Trademarks